US012779176B2

(12) United States Patent
Hiorth et al.

(10) Patent No.: US 12,779,176 B2
(45) Date of Patent: Nov. 3, 2026

(54) STEERABLE INTRODUCER FOR CATHETER DEVICE

(71) Applicant: CARDIOMECH AS, Trondheim (NO)

(72) Inventors: Nikolai Hiorth, Oslo (NO); Hans Emil Hiorth, Trondheim (NO)

(73) Assignee: CardioMech AS, Trondheim (NO)

( * ) Notice: Subject to any disclaimer, the term of this patent is extended or adjusted under 35 U.S.C. 154(b) by 1248 days.

(21) Appl. No.: 17/641,336

(22) PCT Filed: Sep. 8, 2020

(86) PCT No.: PCT/EP2020/075100
§ 371 (c)(1),
(2) Date: Mar. 8, 2022

(87) PCT Pub. No.: WO2021/048140
PCT Pub. Date: Mar. 18, 2021

(65) Prior Publication Data
US 2022/0288356 A1 Sep. 15, 2022

(30) Foreign Application Priority Data
Sep. 9, 2019 (GB) ..................................... 1912941

(51) Int. Cl.
*A61M 25/01* (2006.01)
*A61B 17/00* (2006.01)
(Continued)

(52) U.S. Cl.
CPC .... *A61M 25/0147* (2013.01); *A61M 25/0133* (2013.01); *A61M 25/0136* (2013.01);
(Continued)

(58) Field of Classification Search
CPC ........ A61B 2017/003–00327; A61M 25/0147; A61M 25/0136
See application file for complete search history.

(56) References Cited

U.S. PATENT DOCUMENTS 5,327,905 A 7/1994 Avitall
6,824,550 B1 11/2004 Noriega et al.
(Continued)

FOREIGN PATENT DOCUMENTS

EP 2737922 A1 6/2014
EP 2737922 B1 5/2016
(Continued)

OTHER PUBLICATIONS

English Translation Text of WO-2013008490-A1 (Year: 2013).*
(Continued)

*Primary Examiner* — Jason E Flick
*Assistant Examiner* — Isabella S North
(74) *Attorney, Agent, or Firm* — Norton Rose Fulbright US LLP

(57) ABSTRACT

A steerable introducer for a catheter device is disclosed. The steerable introducer comprises: a body portion (12) having a longitudinal axis extending from a proximal end of the introducer toward a distal end (10) of the introducer, wherein the body portion (12) comprises a flexible distal portion (14) extending to the distal end (10). A hollow (35) is located within a part of the body portion (12) for holding the catheter device during a procedure to introduce the catheter device into the body. There is at least one steering control wire (18, 18) extending axially along the body portion (12) and along at least a part of an axial length of the flexible distal portion (14); and a pair of twisting control wires (16) extending axially along the body portion (12) and along at least a part of an axial length of the flexible distal portion (14). The steering control wire (18, 18') has a distal end that is fixed to the flexible distal portion (14) at a first point (23, 23') in a first axial and circumferential position on the flexible distal portion (14), with the introducer being arranged to allow for tension on the at least one steering control wire (18, 18') to
(Continued)

cause a curvature of the flexible distal portion (14). The pair of twisting control wires 16 each have a distal end, with the twisting control wire distal ends (24) being fixed to the flexible distal portion (14) at second and third points (24, 26) at respective second and third axial and circumferential positions on the flexible distal portion (14), with the circumferential position of the twisting control wire distal ends being different from each other as well as different from the circumferential position of the steering control wire (18, 18). The introducer is arranged to allow for variations in relative tension between the pair of twisting control wires (16) to cause twisting of the flexible distal portion (14).

20 Claims, 8 Drawing Sheets

(51) Int. Cl.
*A61B 18/14* (2006.01)
*A61M 25/00* (2006.01)

(52) U.S. Cl.
CPC .... *A61M 25/0138* (2013.01); *A61M 25/0141* (2013.01); *A61M 25/0152* (2013.01); *A61B 2017/003* (2013.01); *A61B 2017/00309* (2013.01); *A61B 2017/00327* (2013.01); *A61B 2017/00867* (2013.01); *A61B 18/1492* (2013.01); *A61M 25/005* (2013.01); *A61M 25/0144* (2013.01); *A61M 2025/015* (2013.01); *A61M 2025/0161* (2013.01); *A61M 2205/0216* (2013.01); *A61M 2207/00* (2013.01); *A61M 2210/125* (2013.01)

(56) References Cited

U.S. PATENT DOCUMENTS

| | | | | |
|---|---|---|---|---|
| 7,056,314 | B1 * | 6/2006 | Florio | A61M 25/0147 604/95.01 |
| 7,081,121 | B2 | 7/2006 | Muramatsu | |
| 7,374,553 | B2 | 5/2008 | Koerner et al. | |
| 8,523,808 | B2 | 9/2013 | Selkee | |
| 8,894,610 | B2 * | 11/2014 | Macnamara | A61M 25/0147 604/95.04 |
| 9,138,565 | B2 | 9/2015 | Schwager et al. | |
| 9,901,710 | B2 | 2/2018 | Kassab et al. | |
| 10,022,521 | B2 | 7/2018 | Knudson | |
| 10,426,557 | B2 | 10/2019 | Amiri et al. | |
| 10,531,884 | B2 | 1/2020 | Katoh et al. | |
| 10,653,862 | B2 | 5/2020 | Winston et al. | |
| 10,773,053 | B2 | 9/2020 | Ranum | |
| 10,799,675 | B2 | 10/2020 | Khuu et al. | |
| 10,799,676 | B2 | 10/2020 | Khuu et al. | |
| 10,799,677 | B2 | 10/2020 | Khuu et al. | |
| 10,835,714 | B2 | 11/2020 | Khuu et al. | |
| 2004/0215139 | A1 | 10/2004 | Cohen | |
| 2005/0288627 | A1 * | 12/2005 | Mogul | A61M 25/0136 604/95.04 |
| 2006/0241564 | A1 * | 10/2006 | Corcoran | A61M 25/0147 604/523 |
| 2008/0029572 | A1 * | 2/2008 | Shelton | A61B 17/072 227/175.1 |
| 2008/0140101 | A1 * | 6/2008 | Carley | A61B 17/320758 606/159 |
| 2010/0004508 | A1 | 1/2010 | Naito et al. | |
| 2011/0098531 | A1 * | 4/2011 | To | A61B 17/0218 600/114 |
| 2012/0004668 | A1 * | 1/2012 | Wallace | A61B 34/20 606/130 |
| 2016/0051796 | A1 * | 2/2016 | Kanemasa | A61M 25/0136 604/95.04 |
| 2018/0028177 | A1 | 2/2018 | Van Oepen et al. | |
| 2018/0071487 | A1 | 3/2018 | Khuu et al. | |
| 2018/0263764 | A1 | 9/2018 | Manash et al. | |
| 2018/0289436 | A1 | 10/2018 | Jorgensen | |
| 2019/0083747 | A1 | 3/2019 | Khuu et al. | |
| 2019/0192820 | A1 | 6/2019 | Olson et al. | |
| 2020/0324077 | A1 | 10/2020 | Knutson et al. | |
| 2021/0045770 | A1 | 2/2021 | Savastano et al. | |

FOREIGN PATENT DOCUMENTS

| | | | | |
|---|---|---|---|---|
| KR | 101376374 B1 | 3/2014 | | |
| KR | 101598277 B1 | 2/2016 | | |
| WO | WO-9410897 A1 * | 5/1994 | | A61B 1/0052 |
| WO | WO-2013008490 A1 * | 1/2013 | | A61M 25/0136 |
| WO | WO 2019/157303 | 8/2019 | | |
| WO | WO 2020/077337 | 4/2020 | | |
| WO | WO 2020/172224 | 8/2020 | | |

OTHER PUBLICATIONS

Examination Report under Section 18(3) from the Intellectual Property Office of the United Kingdom issued in corresponding Patent Application No. GB1912941.0 dated Jan. 7, 2021.
International Search Report and Written Opinion issued in International Application No. PCT/EP2020/075100 dated Jan. 22, 2021.
Search Report under Section 17 from the Intellectual Property Office of the United Kingdom issued in corresponding Patent Application No. GB1912941.0 dated Jan. 30, 2020.

* cited by examiner

STEERABLE INTRODUCER FOR CATHETER DEVICE

CROSS-REFERENCE TO RELATED APPLICATIONS

This application is a national phase application under 35 U.S.C. § 371 of International Application No. PCT/EP2020/075100 filed 8 Sep. 2020, which claims priority to Great Britain Patent Application No. 1912941.0 filed 9 Sep. 2019. The entire contents of each of the above-referenced disclosures is specifically incorporated by reference herein without disclaimer.

The present invention relates to a steerable introducer for a catheter device, such as a catheter device for conducting a surgical operation within the heart.

It is known to use catheter devices for various medical purposes including surgical operations for implantation of medical devices. In this context a catheter device may be a medical device introduced into the body via a catheter arrangement. WO2016/042022 discloses an example of a catheter device for an operation within the heart to implant an artificial heart chord. When introducing such catheter devices into the body the surgeon needs to be able to accurately steer them through the body and to a target site. For example, the catheter device of WO2016/042022 may be introduced via a transaortic approach, which involves passing the device through the aorta and into the heart. A steerable introducer is typically used for this procedure. Alternatively, the device may be introduced via a transseptal approach, where the introducer approaches the target site through the venous system, across the septum separating the right and left atrium, and then in toward the mitral valve. This approach can involve large anatomical variations and a complex curvature is required to align with the mitral valve plane.

Known steerable introducers typically have a cylindrical form with a hollow interior for holding a catheter device, which may include a medical instrument and/or medical implants as with the example given in WO2016/042022. The introducer has a flexible distal portion that is steerable via the use of control wires with, for example, one or more control wires running along a side of the flexible distal portion and attached to the distal end of the introducer. Applying tension to such a control wire will tend to shorten the associated side of the flexible portion and thus generate a curve in the introducer, allowing it to be steered. Releasing the tension will allow the flexible distal portion to return to its resting position due to elasticity therein and/or via the use of a straightening wire that pulls the flexible distal portion back to a straight configuration. Rotations of the introducer along its axis will give further control of the direction of the distal end.

Viewed from a first aspect, the invention provides a steerable introducer for a catheter device, the steerable introducer comprising:

a body portion having a longitudinal axis extending from a proximal end of the introducer toward a distal end of the introducer, wherein the body portion comprises a flexible distal portion extending to the distal end;

a hollow within a part of the body portion for holding the catheter device during a procedure to introduce the catheter device into the body;

at least one steering control wire extending axially along the body portion and along at least a part of an axial length of the flexible distal portion; and a pair of twisting control wires extending axially along the body portion and along at least a part of an axial length of the flexible distal portion;

wherein the at least one steering control wire has a distal end that is fixed to the flexible distal portion at a first point in a first axial and circumferential position on the flexible distal portion, with the introducer being arranged to allow for tension on the at least one steering control wire to cause a curvature of the flexible distal portion; and wherein the pair of twisting control wires each have a distal end, with the twisting control wire distal ends being fixed to the flexible distal portion at second and third points at respective second and third axial and circumferential positions on the flexible distal portion, with the circumferential position of the twisting control wire distal ends being different from each other as well as different from the circumferential position of the steering control wire, and with the introducer being arranged to allow for variations in relative tension between the pair of twisting control wires to cause twisting of the flexible distal portion.

Thus, with this arrangement the introducer is both steerable and also twistable, such as to create an angling of the distal end whilst the flexible distal portion is curved and optionally a side-to-side panning motion with a consistent angle of the distal end. This can allow for the introducer to fit with complex anatomy and to approach a target site through a convoluted route, which still being able to adequately target the deployment of the catheter device, for example in the case of repair within the mitral space as with the catheter device of WO2016/042022, using just two shafts, being the introducer shaft and separately the shaft of the catheter device. It is important to realise that repair devices for the mitral space generally consist of three shafts, with an introducer, a quad (steerable) shaft and a device shaft. It is beneficial from many perspectives to have as few shafts as possible (e.g. ease of production, ease of use, and reduced risk of failure including both device failure and decreased risk to the patient). The steerable introducer of the first aspect can allow for repairs in the mitral space using only two shafts.

The flexible distal portion can be subject to a curvature within a plane under the influence of the steering control wire, which can be paired with a rotation of the introducer in the manner described above to steer it to a target site, such as by navigation through blood vessels. In addition, the ability to also apply twisting forces via the pair of twisting control wires allows for a finer control of the location and orientation of the distal end of the introducer, and hence of the location of the catheter device as it is deployed. Advantageously, the distal end of the introducer can be moved via the twisting movement simultaneously with the steering movement, so that the distal end may shift out-of-plane from the plane of the curvature that would be the result of tension on the steering control wire alone. With only a steering input the distal flexible portion of the introducer would curve in a plane, whereas with a steering and a twisting input the curvature defines a more complex shape along a three dimensional surface. An added twisting movement can have significant advantages when the correct placement of the distal end is of importance for correct targeting of the catheter device, such as for ensuring correct targeting of the mitral valve for the device of WO2016/042022.

The pair of twisting control wires terminate with their ends fixed at different circumferential positions in order to allow for differences in tension on the twisting control wires to generate a twisting action for the flexible distal portion. The ends of the twisting control wires may be attached to a distal end of the flexible distal portion, or they may be spaced slightly apart from the distal end. Attaching the twisting control wires close to the distal end may increase the twisting effect. In some examples the axial position of the twisting control wire distal ends is about the same (or may be the same) and, for example, the ends may be fixed at the same distance along the flexible distal portion, such as at the distal end thereof. It will be appreciate that although a twisting motion can be generated with a differing axial position for the twisting control wires it is preferred to have their ends fixed at the same axial position as this means that the twisting effect is more proportionate in terms of the effect of tension on one wire or the other.

The ends of the twisting control wires are separated in their circumferential position, and it will be appreciated that any amount of separation will generate some twisting effect when combined with a steering input from the steering control wire, which is at another circumferential position. In example embodiments the circumferential separation of the ends of the twisting control wires is between 5-40% of the circumferential extent of the flexible distal portion, for example with a circular cross-section of the flexible distal portion the distal ends of the twisting control wires may be spaced apart on the circular circumference with a spacing between 18-144 degrees. The spacing may for example be between 10-25% of the circumferential extent of the flexible distal portion.

The pair of twisting control wires have their ends at a different circumferential position to the end of the steering control wire. The ends of the twisting control wires may be placed symmetrically or asymmetrically with the end of the steering control wire. A symmetrical arrangement may aid controllability by making the effect of varying tension in the twisting control wires more proportionate to the amount of twisting movement. An asymmetric arrangement can enhance the ability to form more complex shapes, with the asymmetric positioning of the wires optionally being selected with a particular deployment shape in mind.

Thus, with a symmetric arrangement the ends of the twisting control wires may be at circumferential positions that are spaced apart from the end of the steering control wire by the same distance in opposite directions around a circumference of the flexible distal portion. In the case of a circular cross-section of the flexible distal portion the distal ends of the twisting control wires may be spaced apart on the circular circumference with a distance of 180 degrees ±X degrees. X may be between 9-72 degrees if the 5-40% range above is applied. If the distal ends of the twisting control wires are in symmetrical circumferential positions and also at the same axial position then controllability is further improved.

The pair of twisting control wires may extend in parallel along the flexible distal portion, as well as optionally in parallel along some or all of the main body of the introducer. The steering control wire may also be in parallel with the twisting control wires. Each wire may be parallel with the longitudinal axis of the introducer. Alignment of the wires can avoid unwanted or unexpected forces that might create unpredictable twisting effects. However, in some instances the wires might be at an angle to one another and/or not aligned with the longitudinal axis of the introducer.

The control wires may be located at an outer part of the flexible distal portion, such as within an outer circumferential wall thereof. The control wires may also be located at an outer part of the main body. This allows for other devices and mechanisms to occupy the space at the inner part of the introducer, so that the hollow for holding the catheter device, which may occupy at least some of the inner part of the introducer, is not obstructed by the control wires for twisting and steering. It will be appreciated that there may be a greater degree of freedom in the paths of the control wires at a proximal end of the introducer and hence the control wires may be at an outer part of the introducer, such as along a circumferential wall, for a first section of the introducer at the distal end thereof, including the flexible distal portion, with the control wires not necessarily being at an outer part for a second section of the introducer at the proximal end thereof. In that second section the control wires may move within the introducer, for example.

Each of the control wires may be placed inside composite tubing. Each of the control wires may be housed within a respective composite tube. The composite tubing may be reinforced braided micro tubes. The composite tubing may reduce friction of the wire when it is actuated, in either steering or twisting of the introducer, as appropriate. The composite tubing may assist in providing smoother movement of the introducer, such that finer motor control of the introducer is possible. Housing and/or placing the control wires within composite tubing may result in the introducer being easier to manufacture. Housing and/or placing the control wires within composite tubing may help prevent other components interfering with the control wires, and hence may improve reliability of the device.

The control wires may extend along the entire length of the control wires. The ends of the control wires may be exposed, such that they are attached to an end of the flexible distal portion, or spaced slightly apart from the end of the flexible distal portion, as required. The composite tubing may be interrupted along the length of the control wires at intervals, such that the control wires may be attached to the flexible distal portion as required, e.g. along it rather than simply at an end of it. By exposing the control wires only where necessary, actuation of the control wires may be communicated to the introducer whilst reducing friction between the control wires and the introducer where there is no such communication.

The introducer may include a controller for controlling the tension in the steering control wires and/or in the twisting control wires. The controller may be arranged to control relative tension between the two twisting control wires. It will be appreciated that an accurate control of a twisting motion of the distal end may require the twisting control wires to both be in tension with the user being able to alter the tension between the two wires. The controller may hence be arranged to allow the user to reduce the tension in a first twisting control wire and simultaneously increase the tension in a second twisting control wire, or vice versa.

The controller may include a twisting control mechanism comprising: a tensioner for applying tension to both of the pair of twisting control wires, and a tension balancer for varying the relative tension of the two twisting control wires. The tensioner may apply a tensioning force along the length of the two twisting control wires, such as by a pulling force applied to a proximal end of each wire. The tension balancer may vary the relative tension by adjusting a lateral force on each of the two twisting control wires, i.e. a force applied in a direction that extends perpendicular to the longitudinal extent of the wires at the controller. The tension balancer may hence vary the tension by a force that uses the principle of bow tension, where variation in a lateral displacement of the wire changes the longitudinal tension.

The twisting control mechanism may include lateral restraints spaced apart from the tension balancer in the longitudinal direction of the wires. The lateral restraints are advantageously provided to restrict lateral movement of the wires in the direction of the lateral force applied by the tension balancer. For example, the lateral restraints may include fixed restraints, e.g. pins, at two points spaced apart to either side of a point where the tension balancer applies a lateral force. Such fixed restraints may prevent any movement in the direction of the lateral force applied by the tension balancer at those points, such that the lateral force from the tension balancer distorts the respective twisting control wire into a V-shape. This hence allows for efficacious creation of the required bow tension effect. It will be appreciated that the geometry and dimensions of the twisting control mechanism can be varied in order to adjust a mechanical advantage that arises via the bow tension effect, for example by varying the spacing between the lateral restraints. This can aid ease of use and design freedom by allowing a small input force over a relatively large distance to create a larger change in relative tension for the twisting control wires, over a relatively small distance.

In one example the tension in the pair of twisting control wires is controlled by the tension balancer through a sledge in contact with both of the twisting control wires, where a sliding motion of the sledge in a first direction will increase a lateral displacement of the first twisting control wire whilst decreasing the lateral displacement of the second twisting control wire, and where a sliding motion of the sledge in a second direction will increase a lateral displacement of the second twisting control wire whilst decreasing the lateral displacement of the first twisting control wire. The first and second directions may be parallel and opposite. The first and second directions extend away from the longitudinal extent of the twisting control wires at the controller in order that the contact of the sledge with the wires can apply a lateral force. The sledge may be actuated by a control input as discussed below, for example a knob that turns a screw thread to slide the sledge in the first direction or the second direction. In the example embodiment the first and second directions each extend perpendicular to the longitudinal extent of the control wires at the controller.

The controller may include control inputs for manual control of the tension in the wires, via manual actions of a user, for example there may be a twisting control input and a steering control input. Where multiple steering control wires are used then there may be a corresponding plurality of steering control inputs. The control inputs may take the form of a knob or lever, and may provide an input to control relative tension between the two twisting control wires, such as via a twisting control mechanism with a tension balancer as discussed above. The control inputs may be rotating inputs that move a screw thread and/or a worm wheel to apply a force to the wire(s).

To ensure that the control wires remain taut, one or more constant tension device may be used within the introducer, and there may be one or more constant tension device(s) provided as a part of the controller. A constant tension device may be used to ensure that even during deformation of the steerable introducer there is a required minimum tension force in one or more of the control wires at all times. Constant tension devices may be provided for each of the control wires and/or a single constant tension device may be used to ensure a minimum tension for each of the control wires. An example of a constant tension device includes but is not limited to a constant force spring.

Some of the operations that these controller is designed to perform may require a limited force. To aid the user in knowing when such a force is applied to these components, a clutch can be utilised that releases when a certain torque is reached. In that case, it may be valuable to allow the user to know when the clutch is engaging. The clutch may therefore be a ratchet clutch, whereby the operator may be notified that the clutch is engaged due to the clutch producing audible clicks. Alternatively, an O-ring squeeze clutch may be used. In this example, the clutch releases when a certain torque is reached to prevent further force being applied to the control wires with which it is engaged.

The flexible distal portion may be elastically flexible so that it returns elastically to a resting position when no tension is applied to the steering control wire or the twisting control wires. The resting position may be generally straight and in alignment with the longitudinal axis of the main body. In that case, when no forces are applied to the flexible distal portion, such as from the control wires or from external sources, then it will return to a straight configuration. Alternatively, the flexible distal portion may be arranged to have a curve and/or a twist in its resting position such that a tension must be applied to one or more of the control wires in order to move the flexible distal portion into a straight configuration. For example, where the flexible distal portion comprises heat set elastic elements as discussed below, then these may be heat set into a curved and/or twisted configuration. The flexible distal portion may have a resting position that has a proportion of a curve and twist required for deployment of the catheter device. This may be 20-60% of a required curve and twist, such as about 40% of the required curve and twist. Thus, the flexible distal portion may have a resting position in which it is curved and optionally twisted partway toward an intended configuration in use for deployment of the catheter device. The intended configuration may comprise a curve of the flexible distal portion through about 180 degrees with a first curvature along the first 90 degrees of bend, and a second, tighter, curvature along the second 90 degrees of bend. It will be understood that the twisting of the flexible distal portion could be overlaid on this curved shape to further adjust the location and angle of the distal end. The first curvature and the second curvature may be out of plane with one another, for example with a twist applied to the second curvature compared with the orientation/plane of the first curvature. The resting position may include a curvature of 20-60% of this intended configuration, for example a curve through an angle in the range 36 to 108 degrees, optionally with a proportion of the required twist, where present.

The flexible distal portion may have a different elasticity at different axial positions and/or different elasticity with respect to bending in different directions. Thus, the stiffness of the flexible distal portion may be different for different locations along the length of the flexible distal portion. Alternatively, or additionally, the stiffness of at least a section of the flexible distal portion may be different with respect to bending in different directions. In some examples the flexible distal portion has a first flexible section at the distal end of the introducer and a second flexible section between the first flexible section and the main body, with each flexible section having a different stiffness. Optionally there may be a third flexible section, or more than three sections of differing stiffness.

Alternatively, or in addition the flexible distal portion may be arranged with a varying stiffness at different points around the circumference of the flexible distal portion. For example, this can be achieved by the use of stiffer or more flexible materials as desired. In some examples a part of the circumference that forms the outer curve in a deployed configuration of the flexible distal portion may be stiffer than a part of the circumference that forms the inner curve. This gives the advantage of shifting compression to the inner curve. In the alternative a stiffer inner curve may be used to shift the elongation to the outer curve.

The stiffness of the flexible sections may be relatively lower toward the distal end of the device. Thus, in the case set out above the first flexible section may be less stiff, i.e. more flexible, than the second flexible section. This gives a greater degree of maneuverability for the distal end, where a finer degree of movement is beneficial. Alternatively or additionally there may be different degrees of elasticity with reference to curve and twisting, such as by having the first flexible section arranged for a greater ease of twisting, whilst the second flexible section is stiffer when twisted, and may thus be relatively rigid so that the first flexible section both twists and curves, whilst the second flexible section curves with lesser twisting. This may be achieved by the second flexible section having a first stiffness with respect to bending forces applied in a first direction and a second, different, stiffness with respect to bending forces applied in a second direction. The second direction may be a direction that is perpendicular to the first direction. Hence, for example, the second flexible section may be relatively more flexible in a side to side direction and relatively more rigid in a front to back direction, wherein the front to back direction is perpendicular to the side to side direction. In some implementations the second flexible section may be able to bend relatively easily in the side to side direction, with the second flexible section being generally rigid in the front to back direction. In contrast, the first flexible section may be able to bend relatively easily in all directions, optionally having a similar elasticity in relation to bending in any direction.

The relative stiffness of the flexible sections may be varied using different stiffnesses of material. The flexible distal portion may comprise an elastic material forming an outer wall thereof, such as an elastic polymer material. Differing stiffnesses or differing thicknesses of elastic material may be used to vary the relative stiffness of first and second flexible sections of the flexible distal portion. For example, the main body of the steerable introducer may comprise an elastic material having a Shore hardness of 72D, whereas the first flexible section may comprise an elastic material having a Shore hardness of 25D and the second flexible section may comprise an elastic material having a Shore hardness of 40D.

The flexible distal portion may comprise elastic elements such as metal and/or polymer elements, for example spring type elements. The elastic elements may provide a "backbone" for the flexible distal portion, for example an internal shaping and reinforcing structure, which may be embedded in an elastic material as discussed above, such as an elastic polymer material. Thus, a distal segment of the flexible distal portion may comprise a reinforced polymer backbone surrounded with an elastic polymer material. The distal segment may be the first section discussed further below. The elastic elements may have the form of a tube with cuts permitting bending of the tube, such as an array of slots cut along the length of the tube. One way to form such a tube is by laser cutting of a full tube. The tube may be formed by heat setting a suitable metal, such as nitinol or stainless steel, or other elastic material, such as a reinforced polymer material. The tube may be formed with a resting position that incorporates some curve and/or twist as discussed above.

A liner may be situated between the backbone for the flexible distal portion and the surrounding elastic polymer material. The liner may be a polymer lining, such as Pebax® coated PTFE. The liner may act as a skin, which increases adhesion between the flexible backbone and the surrounding elastic polymer.

In some cases there are advantages if at least the first flexible section of the flexible distal portion is less visible to imaging systems, and hence advantages if the use or metal is minimised where possible. Thus, the first flexible section may comprise a first part of the elastic element that is made of a less visible material for an imaging system of interest, i.e. a material that casts less shadow in relation to the imaging system, such as a more sonolucent material where ultrasound imaging is expected to be used. The first flexible section may comprise a first part of the elastic element formed from a polymer material, such as a fibre reinforced polymer material. A similar material may be used for a second part of the elastic element for the second flexible section, optionally with a differing stiffness, or alternatively a metal may be used for that second part. The second flexible section is not as close to the deployment location for the catheter device and hence there is less risk of obstructing the physician's field of view even if metal is used in that section.

Alternatively, a radiopaque polymer may be utilised in the distal portion. This may assist in visualising the distal portion of the catheter device when introduced into the body. The polymer may be radiopaque to X-rays and other similar imaging radiation techniques, such as fluorescence imaging. It may be desired to see the end of the distal portion when imaging the steerable introducer in use. As such only an end of the distal portion may be formed of radiopaque polymer. For example, where various sections of flexibility are utilised, the first flexible section may be more opaque to radiation than the second or third sections. Additionally or alternatively, a band of radiopaque material may be located at the end of the distal portion. The opaqueness of the distal portion to various radiation may be varied as necessary, depending on the imaging techniques a physician may wish to use during use of the catheter device.

The tube may be formed with differing geometries of cuts at different points, such as to contribute toward different elasticity for a first flexible section and a second flexible section as discussed above. Thus, in one example the flexible distal portion may include a tube with cuts permitting bending of the tube at the first flexible section and the second flexible section, with the cuts being configured to provide one or more of: an increased elasticity for the first flexible section in comparison to the second flexible section; an increased elasticity for bending of the second flexible section in a side to side direction in comparison bending of the second flexible section in a front to back; and/or relatively higher ease of bending in all directions of the first flexible section, with relatively lower ease of pending for at least the front to back direction of the second flexible section.

The main body is advantageously flexible but in general may be arranged to flex passively in response to external forces, whilst the steering or twisting effect from the control wires primarily impacts on the form of the flexible distal portion. It is advantageous for the main body to be sufficiently flexible to follow the distal end through the body toward the target site without putting undue strain on the patient, such as when passing through blood vessels without the risk of damage to the blood vessels or the surrounding body tissues. In some examples the stiffness of the main body is greater than that of the flexible distal portion, i.e. greater than the stiffness of each flexible section thereof.

This ensures that the steering and twisting control applies primarily to the flexible distal portion without excessive bending or twisting of the main body in reaction to the control wire tensions.

It will be understood that in this context the stiffness and elasticity of the device relates to bending motions that tend to curve the flexible distal portion (or the main body) along the length thereof, rather than stiffness with respect of tensile or compressive loads along the length, although the two may be related. The main control mechanism for the position of the distal end of the introducer is the application of curvature to the axis of the introducer, in particular via control of curvature and twisting at the flexible distal portion, rather than any kind of control of the axial length and optionally with minimal or no control of curvature of the main body, which may be supported primarily by the vessels of the body within which it is placed. Generally the introducer is arranged to be more rigid along the axial length of the main body than the flexible distal portion, which is relatively more elastic.

There may be more than one steering control wire to allow for a greater control of the degree of curvature. For example, there may be two or more steering control wires, which may extend to a similar circumferential position but be fixed at different axial positions. Thus, the steering control wires may have different lengths along the axis of the introducer with the distal ends of the steering control wires being fixed to the flexible distal portion at different axial positions. This can allow for a differing degree of curvature along the axial extent of the flexible distal portion, such as a tightening curve along the length thereof. It may also allow for a panning motion with the distal end of the device moving laterally without any change in angle, e.g. panning closer and further from the main body of the introducer when in a curved configuration. A first steering control wire may have a distal end fixed to the distal end of the flexible distal portion, or close to the end. This first steering control wire may have an axial position that is similar to that of the pair of twisting control wires. A second steering control wire may have a distal end fixed to the flexible distal portion at a different axial position to the distal end of the first steering wire, and optionally at a different one of the flexible sections in the case where the stiffness of the flexible distal portion varies along its length.

The two or more steering control wires may be aligned with each other. Thus, they may be parallel and preferably also aligned in terms of their circumferential position. The steering control wires may be placed adjacent one another and thus may run effectively concurrently along at least a distal part of the main body and along the flexible distal portion, until the respective distal ends of the steering control wires, which are advantageously at different axial positions as noted above.

The flexible distal portion and/or the main body may be generally cylindrical in shape. The flexible distal portion may include a flexible cylindrical outer wall at the outer circumference thereof, preferably a cylindrical wall that defines the entirety of the flexible distal portion. The body portion may be cylindrical, and the diameter of the introducer may be generally similar along its length such that the body portion as well as the flexible distal end have a similar diameter. In example embodiments the outer diameter of the introducer is in at least 7 mm, such as about 8 mm or larger.

The hollow may have a width in the range 6-8 mm in order to receive a catheter device of a slightly smaller width, for example 6-7 mm. For example the hollow may have a width of at least 6.5 mm or about 6.7 mm in order to hold a catheter device with outer diameter of about 6 mm. The hollow may have a generally cylindrical shape in order to fit a generally cylindrical catheter device, in which case the widths referenced above may be diameters.

A liner may be situated within the flexible distal portion. The liner may extend around the inner circumference of the flexible distal portion and along the flexible distal portion. The liner may define the hollow. The liner may act as a skin which separates the flexible distal portion and its associated components, such as the control wires and if present the flexible backbone, from any components within the catheter device such as anchors and their associated deployment mechanisms, control wires and/or rods. The liner may be a Pebax® coated PTFE liner.

In a second aspect, the invention provides a cardiac treatment apparatus comprising a steerable introducer as discussed above in relation to the first aspect or any optional feature thereof, along with a catheter device for performing an operation within the heart, wherein the catheter device is housed within the hollow of the steerable introducer. The catheter device may for example be a device for implanting anchors within the heart, such as a device for implanting an artificial chordae as disclosed in WO2016/042022.

Viewed from a third aspect the invention provides a method of manufacture of a steerable introducer as discussed above in relation to the first aspect and the optional features thereof. The method may include providing a body portion with a flexible distal portion as discussed above, including providing a hollow within a part of the body portion for holding the catheter device and arranging the flexible distal portion to allow for curvature and twisting thereof. The method may comprise fitting of the at least one steering control wire and the pair of twisting control wires, including attaching the at least one steering control wire in a position extending axially along the body portion and along at least a part of an axial length of the flexible distal portion, and attaching the pair of twisting control wires in a position extending axially along the body portion and along at least a part of an axial length of the flexible distal portion. The method may comprise fixing a distal end of the at least one steering control wire to the flexible distal portion at a first point in a first axial and circumferential position on the flexible distal portion, with the introducer hence being arranged to allow for tension on the at least one steering control wire to cause a curvature of the flexible distal portion; and fixing the distal ends of the pair of twisting control wires to the flexible distal portion at second and third points at respective second and third axial and circumferential positions on the flexible distal portion, with the circumferential position of the twisting control wire distal ends being different from each other as well as different from the circumferential position of the steering control wire, and with the introducer hence being arranged to allow for variations in relative tension between the pair of twisting control wires to cause twisting of the flexible distal portion.

The method may include providing any of the other features of the steerable introducer discussed above. The method may for example comprise forming the flexible distal portion with a different elasticity at different axial positions and/or different elasticity with respect to bending in different directions. This may be done by manufacturing the flexible distal portion with a first flexible section at the distal end of the introducer and a second flexible section between the first flexible section and the main body. Each flexible section may have a different stiffness and the first flexible section being more flexible than the second flexible section. Alternatively or additionally, the method may include manufacturing the first flexible section with a configuration allowing for a greater ease of twisting, whilst the second flexible section is stiffer when twisted. This may be achieved by the second flexible section having a first stiffness with respect to bending forces applied in a first direction and a second, different, stiffness with respect to bending forces applied in a second direction such that the second flexible section is relatively more flexible in a side to side direction and relatively more rigid in a front to back direction, whereas the first flexible section is able to bend relatively easily in all directions.

The flexible distal portion may comprise elastic elements such as metal and/or polymer elements, for example spring type elements. The elastic elements may have the form of a tube with cuts permitting bending of the tube, such as an array of slots cut along the length of the tube. The tube may be embedded in an elastic material, such as an elastic polymer material. In that case the method may also include moulding the elastic material around the tube. Thus, the method may including cutting a tube to form an elastic element of the flexible distal portion, for example laser cutting of a metal tube or of a fibre reinforced polymer tube. The method may comprise forming differing geometries of cuts at different points along the length of the tube, for example to form the first and section sections with differing configurations as discussed above. The tube may be formed by heat setting a suitable metal, such as nitinol or stainless steel, or by heat setting a suitable polymer material. The tube may be formed with a resting position that incorporates some curve and twist as discussed above.

The invention further extends to the use of the steerable introducer of the first aspect and optional features thereof. This may comprise the use of a catheter device for performing an operation within the heart, wherein the catheter device is housed within the hollow of the steerable introducer, and the method of use hence may include introducing the catheter device into the heart. During use of the steerable introducer the steering control wires are used to control the curvature of the flexible distal portion and the twisting control wires are used to control a degree of twist of the flexible distal portion. This may include the use of a controller as discussed above.

A possible method of use of the steerable introducer comprises:

1. Advancing the introducer sheath with a dilator inside, passing the introducer over a guide wire and into the left atrium.
2. Removing the dilator to release the introducer into a pre-curved configuration, for example 20-60% of an intended deployment position.
3. Advance the device so it is just outside the distal end of the introducer
4. Deploying the catheter device so that the distal end thereof is outside of the introducer.
5. Alignment of the distal end of the introducer and hence of the catheter device by curvature and twisting using the control wires so that the catheter device is pointing straight down into the mitral valve.
6. Advancing the catheter device from the introducer into the mitral valve.

After this step the catheter device can perform the required procedure within the heart, such as the procedure described in WO2016/042022. After the required procedure then the catheter device should be removed from the heart. This may be done by retracting the catheter device and optionally also simultaneously releasing some or all of the curvature and twisting to allow for easier movement of the catheter device, once this will not cause any damage to the heart.

Certain embodiments of the present invention will now be described by way of example only and with reference to the accompanying drawings, in which.

Figure 4:
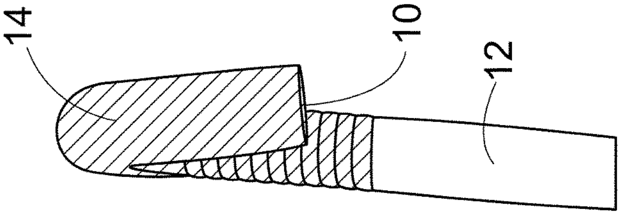
FIGS. 1 to 4 show various views of a flexible distal portion of a steerable introducer with different curvature and twist at the distal end.
Figure 3:
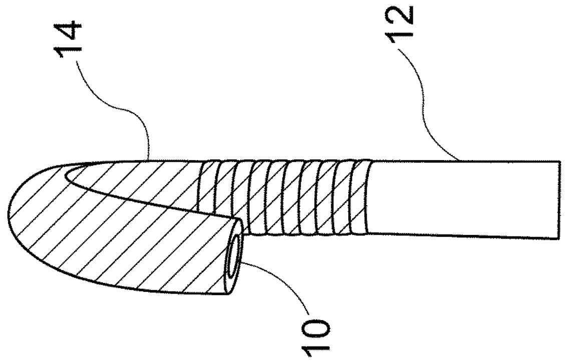
Figure 2:
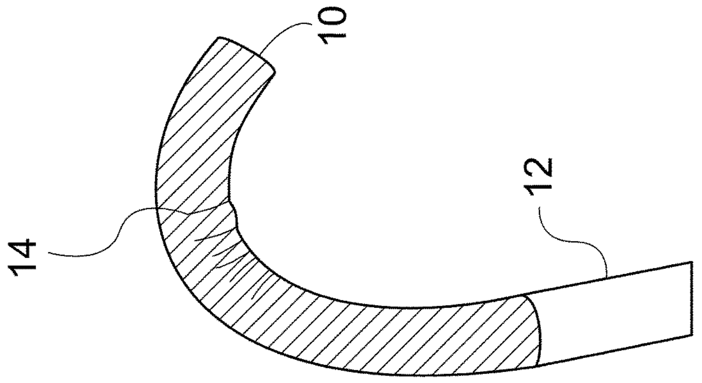
Figure 1:
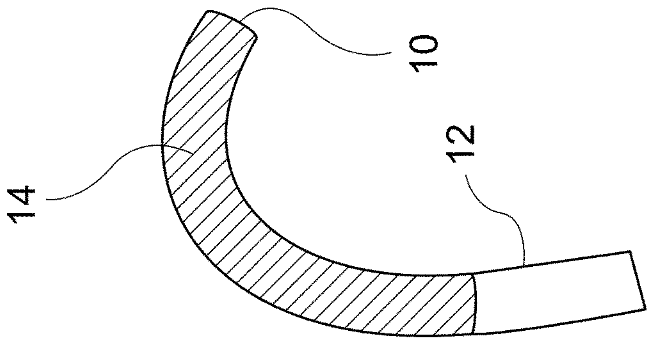

A steerable introducer with both a curving and a twisting capability is shown in various configurations in FIGS. 1 to 4. The introducer has a distal end 10 and a main body 12 (not shown in full). A flexible distal portion 14 is provided at the end of the main body 12, with this flexible distal portion 14 allowing for movement of the distal end 10 using varying degrees of curvature as shown in FIG. 1 and FIG. 2, and also with the addition of a twisting deformation as shown in FIG. 3 and FIG. 4. A catheter device, such as the device of WO2016/042022, can be housed in a hollow within the flexible distal portion 14, with this hollow also extending into the main body 12.

The steerable introducer may be used to introduce such a catheter device into the heart, for example in order to perform a procedure to implant an artificial heart chord as discussed in WO2016/042022. The curvature as shown in FIGS. 1 and 2 can be used to steer the introducer as it passes through blood vessels as well as to locate the distal end 10 at a required position in the heart, for example to direct the catheter device to a required location in the heart when it is deployed from the distal end 10. The twist of the flexible distal portion 14 can be used to more accurately place the distal end 10 with reference to lateral movement such as a movement between the position in FIG. 3 and that in FIG. 4. In addition the ability to twist the flexible distal portion 14 allows for better adjustment of the angle of the distal end 10. It will be seen that in FIG. 3 the distal end 10 is angled differently compared to the angle of the distal end 10 in FIG. 4.

Figure 5:
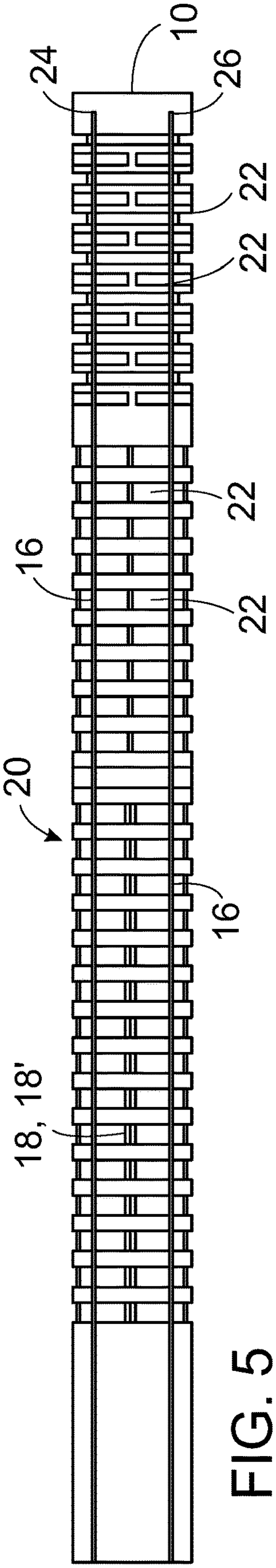
FIGS. 5 to 7 are two side views and a perspective view of an example configuration for an elastic element of the flexible distal portion and the positions of control wires.
Figure 6:
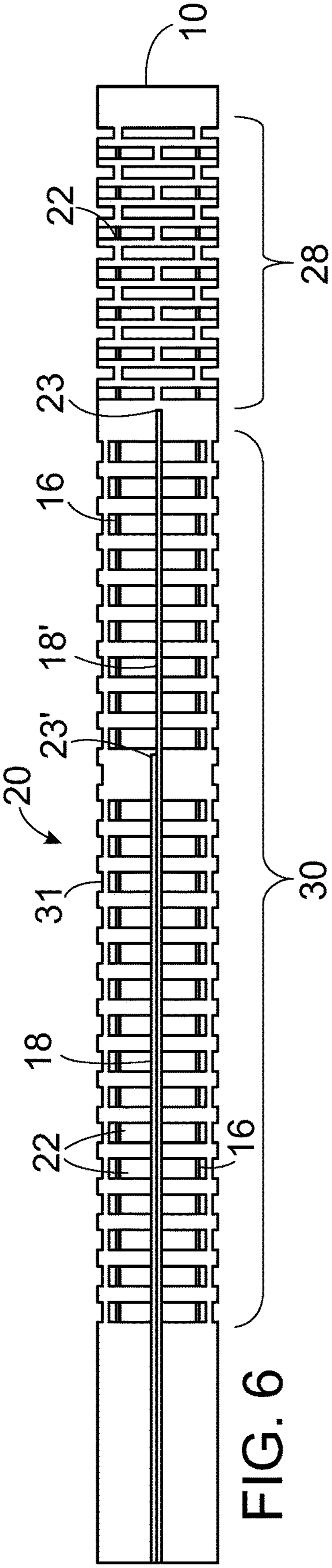
Figure 7:
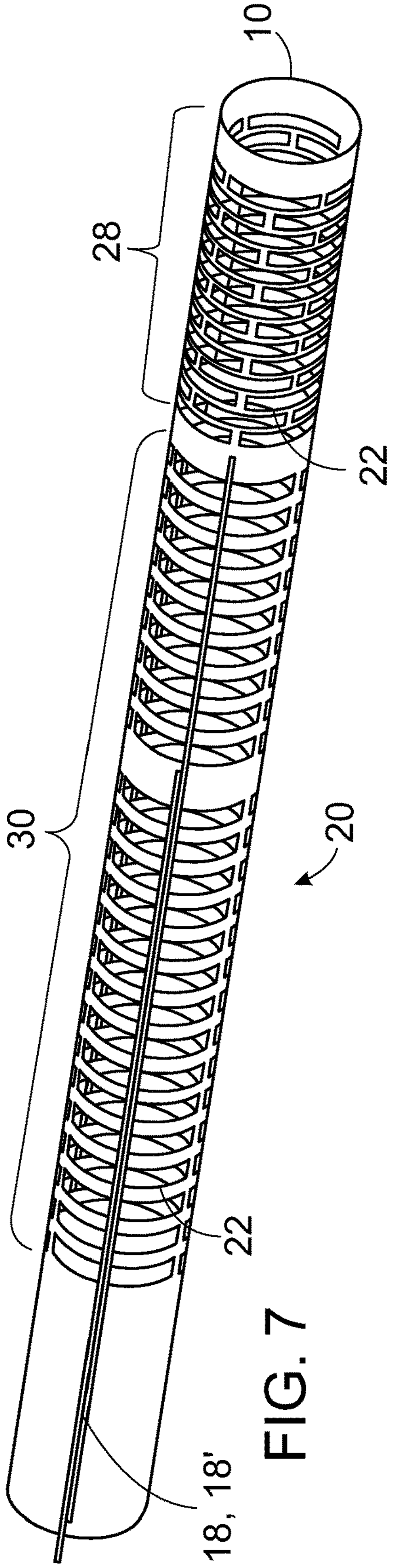

The combined steering and twisting capability is obtained via an arrangement of control wires 16, 18, 18' along with an elastic element 20 within the flexible distal portion 14, acting as a form of "backbone". As shown in FIGS. 5, 6 and 7 the elastic element 20 in an example embodiment is formed of a flexible tube 20 with cuts 22 along its length to provide a required flexibility. The tube 20 may for example be formed from a suitably elastic metal such as nitinol or stainless steel, and/or from a fibre reinforced polymer material, such as PEEK. This example uses a pair of twisting control wires 16 as well as two steering control wires 18, 18'. There is a primary steering control wire 18 that extends to a distal end thereof at first point 23 along the length of the flexible distal portion 14 as well as a secondary steering control wire 18' that extends to a distal end thereof a different point 23' along the length of the flexible distal portion 14, as shown in FIG. 6. The twisting control wires 16 have their distal ends fixed to the flexible distal portion 14 at a second position 24 and a third position 26 at the distal end 10 of the elastic element 20. The first, second and third positions are at different points around the circumference of the flexible distal portion 14 in order to achieve the required control of the curvature and twist thereof. The second position 24 and the third position 26 are at the same point along the axis of the flexible distal portion 14, and are symmetrically spaced either side of the first position 23.

The flexible distal portion 14 is provided with a first flexible section 28 and a second flexible section 30 with different elastic characteristics. The different elastic characteristics may arise in part due to differences in the elastic element 20, which has a corresponding first flexible section 28 and a second flexible section 30. The differences in the elastic element 20 may be differences in material type of thickness. For example the first flexible section 28 may comprise a fibre reinforced polymer and the second flexible section 30 may comprise a metal material. The first flexible section 28 and second flexible section 30 may be formed with cuts 22 of different geometry to provide differing behaviours for the first flexible section 28 and the second flexible section 30 when forces are applied by the control wires 16, 18, 18'. It will be appreciated that the design of the cuts can be varied from that shown whilst achieving a similar effect. In this example the first flexible section 28 is able to flex in all lateral directions, i.e. side to side as well as front to back, since the cuts 22 in the first flexible section 28 provide openings at all points around the circumference. In contrast, the second flexible section 30 has cuts 22 providing openings along the two sides as shown in FIGS. 5 and 6 with a stiffener 31 along the front and back. The stiffener 31 in this example is an uncut portion of the tube running along the length of the second flexible section 30. This makes the second flexible section 30 relatively rigid in relation to bending forces applied in a front to back direction, but relatively flexible in relation to side to side flexing, i.e. into and out of the page with reference to FIGS. 5 and 6.

It will be understood that an increased tension in the steering control wires 18, 18' will tend to reduce the length of the second flexible section 30 and hence impart a curvature to the flexible distal portion 14 as shown in FIGS. 1 and 2. Since the two steering control wires 18, 18' have differing lengths then it is possible to have a varying curvature along the length of the flexible distal portion as shown in FIG. 2. In addition it is possible to have a panning motion of the distal end 10 with a consistent angle of the distal end. The twisting control wires 16 are used to impart a twist to the flexible distal portion 14 and in particular to deform the first flexible section 28, as shown in FIGS. 3 and 4. Varying the relative tension in the two twisting control wires 16 will change the degree of twist. It should be noted that the resting position for the elastic element 20 may not be the straight position as shown in FIGS. 5, 6 and 7. Instead it may be heat set into a deformed position, which is advantageously a position part way toward an intended position for deployment of the catheter device. This deployment position could be similar to that of FIG. 2 for example, and the resting position of the elastic element 20 may be 40% deformed toward such a position. The flexibility of the cutting pattern can also allow for changes in shape and diameter as the catheter device passes through within the hollow 35, which can be seen in FIGS. 9 and 10.

Figure 8:
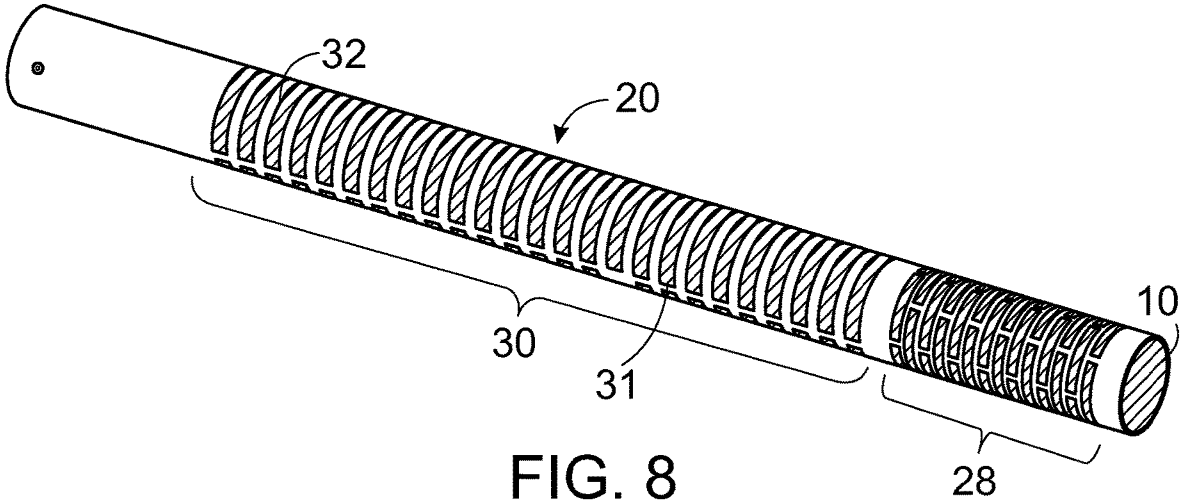
FIG. 8 shows the use of an elastic material in openings of the elastic element.
Figure 9:
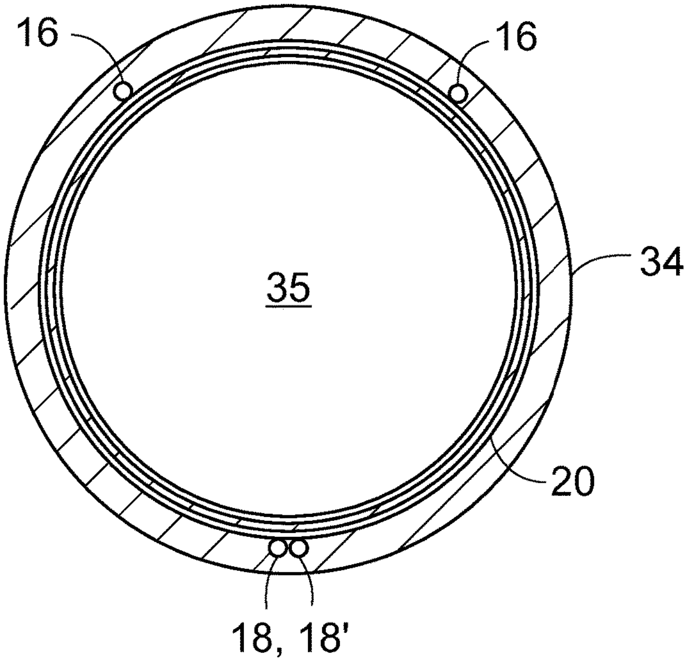
FIG. 9 is a cross-section of an example in which the elastic element is embedded in an elastic material.

The elastic element 20 can be encased in an elastic material, for example an elastic polymer, which may hence comprise elastic material 32 in the cuts 22 as shown in FIG. 8, as well as elastic material 34 surrounding the elastic element 20 as seen in the cross-sectional view of FIG. 9. The elastic material 32, 34 may be a compressible material allowing for deformation with minimal buckling. The composition and/or thickness of the elastic material 32, 34 may vary along the length of the flexible distal portion to vary the flexibility at different points, in particular to contribute to a different elasticity for the first flexible section 28 and the second flexible section 30.

Figure 10:
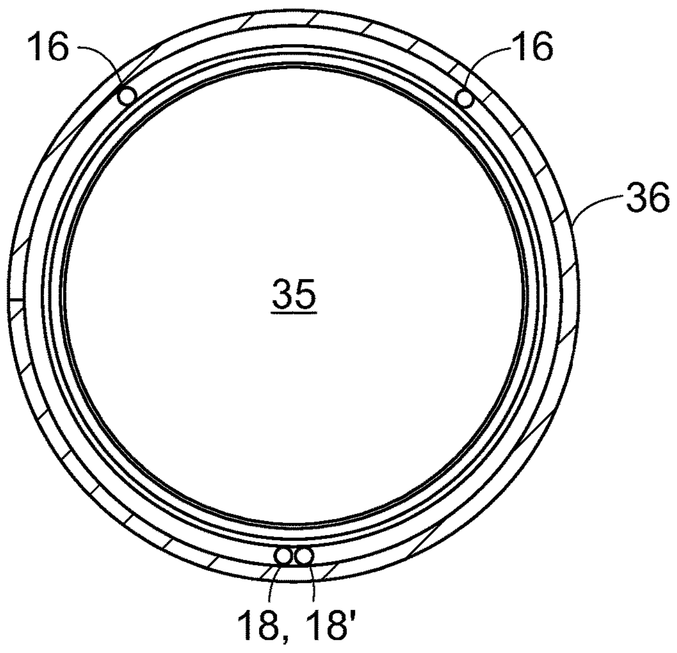
FIG. 10 shows a similar cross-section with the elastic material omitted to allow a coil to be seen.
Figure 11:
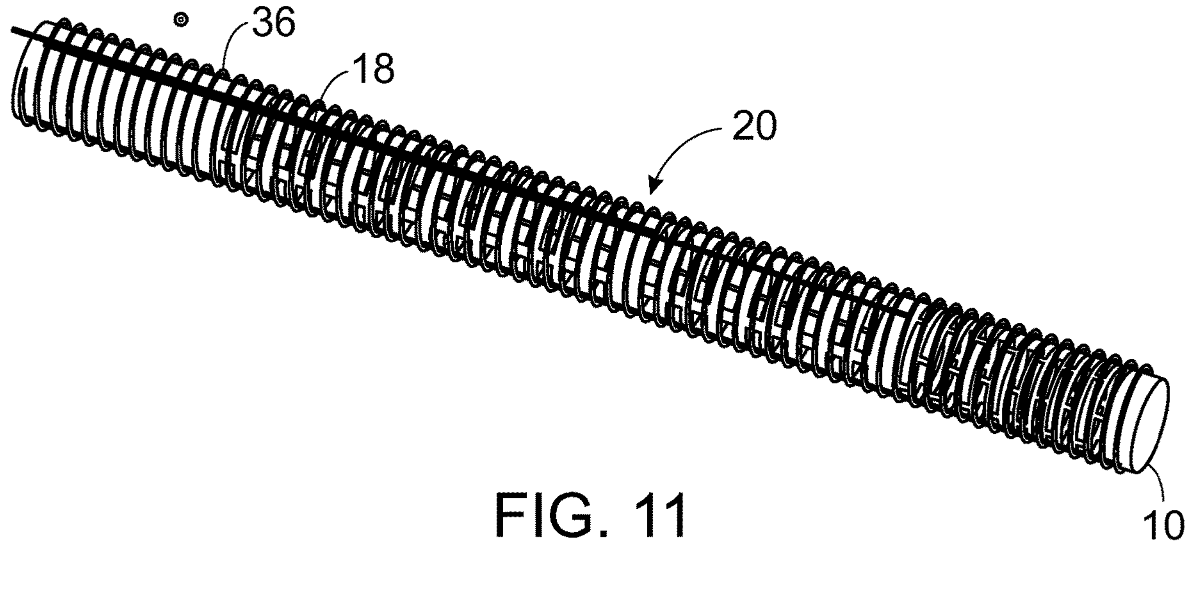
FIG. 11 is a perspective view of the same components as FIG. 10.

The positions of the control wires 16, 18, 18' at the circumference of the elastic element 20 can be seen in FIGS. 9 and 10. FIG. 9 shows the elastic material 34 provided around the outside of the flexible distal portion 14. FIG. 10 shows a flexible coil 36 wrapped around the elastic element 20, and this is also shown in FIG. 11. A flexible coil 36 can optionally be used to add stiffness and to protect the flexible distal portion 14. The coil 36 and the elastic material 32, 34 can be used together. In this example the control wires 16, 18, 18' are placed outside of the elastic element 20, inside the coil 36, and embedded in the elastic material 34. The control wires 16, 18, 18' could alternatively be within the elastic element 20 or outside the coil 36. There may be additional steering control wires for further refinement of the steering control action. Another option is for a straightening wire to modulate the curve.

Figure 12:
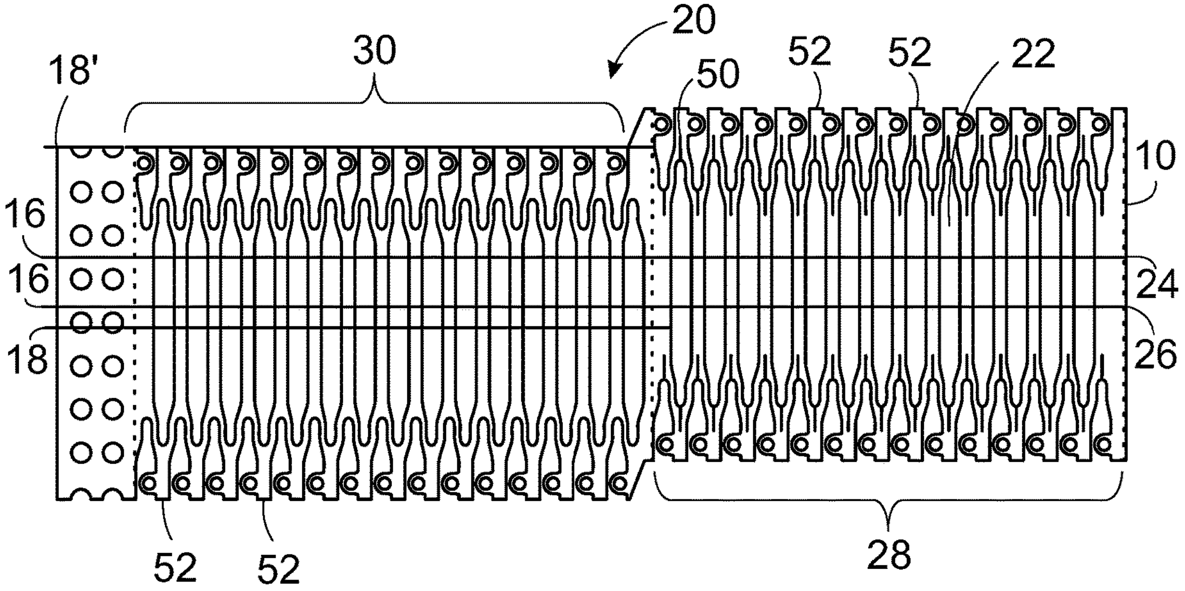
FIG. 12 shows a net for another example for the elastic element and locations of the control wires.
Figure 13:
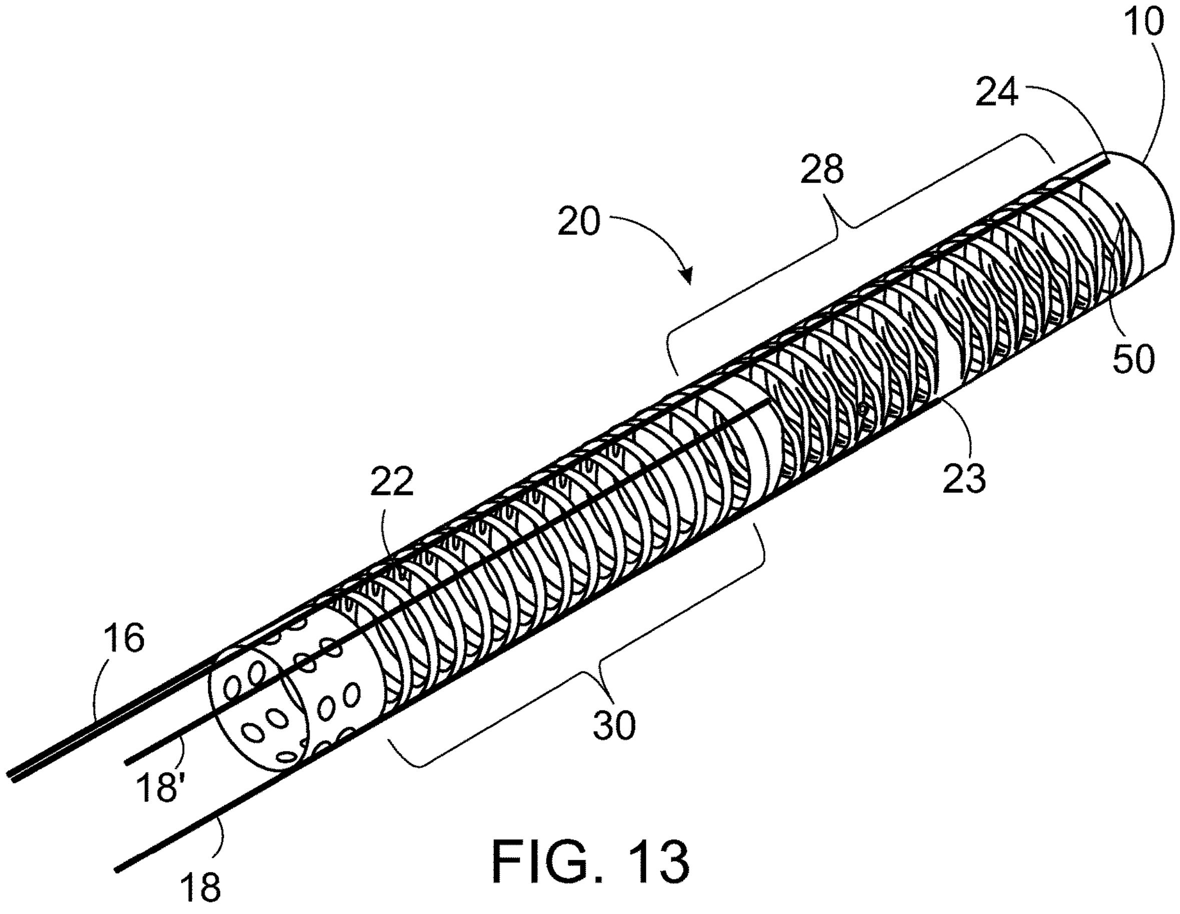
FIG. 13 is a perspective view of a yet further example for the elastic element and locations of the control wires.

FIGS. 12 and 13 show further examples of the form of the elastic element 20, with FIG. 12 showing a cut pattern as a net for a tube, and FIG. 13 showing another example of a tube in perspective view. In both these examples the cuts have a more complex shape than those of the earlier Figures, and in both examples the first flexible section 28 and second flexible section 30 may optionally be made of a reinforced polymer, or of metal. Where differing materials are used for the first flexible section 28 and second flexible section 30 then they can be joined by suitable bonding materials or devices. Slits 50 are used to allow greater flexibility of the first flexible section 28, compared to the second flexible section 30, and these slits are seen as being of particular benefit when a metal tube is used.

As with the prior example, differing stiffnesses of elastic material 32, 34 around the elastic element can be used to contribute to differences in stiffness for the first flexible section 28 and the second flexible section 30, along with differences in the material and cut pattern for the first flexible section 28 and the second flexible section 30. The material selection can in some cases have the largest effect on the stiffness. Where different materials are used then a different stiffness for the first flexible section 28 and the second flexible section 30 can be achieved with the same cut pattern.

Also present in both of the examples of FIGS. 12 and 13 is an asymmetric placement of the twisting control wires 16 compared to the locations of the steering control wires 18, 18'. Thus, the second position 24 and the third position 26 at the distal end 10 of the elastic element 20 are not symmetrically arranged relative to the first position 23 for the steering control wire. Also, with reference to FIG. 12, there is some variation in axial position for the ends of the wires. The arrangement of FIG. 12 may use both pairs of wires 16, 18, 18' for some manner of twisting control, whilst also using both pairs of wires 16, 18, 18' for some manner of steering control. The example of FIG. 12 differs from that of FIG. 13 and the other Figures by reference to fingers 52, which are added at the location of the outer curve in use in order to maintain a smoother surface when in the deflected/curved configuration. Openings within the fingers 52, as well as a generally open cut pattern, allow for good interconnection of the elastic material 32, 34 around the elastic element and with the ptfe liner on the inside of tube, reducing the risk of failure via delamination or other mechanical disengagement of the elastic material and or liner from the tube.

Figures 14A, 14B, 14C:
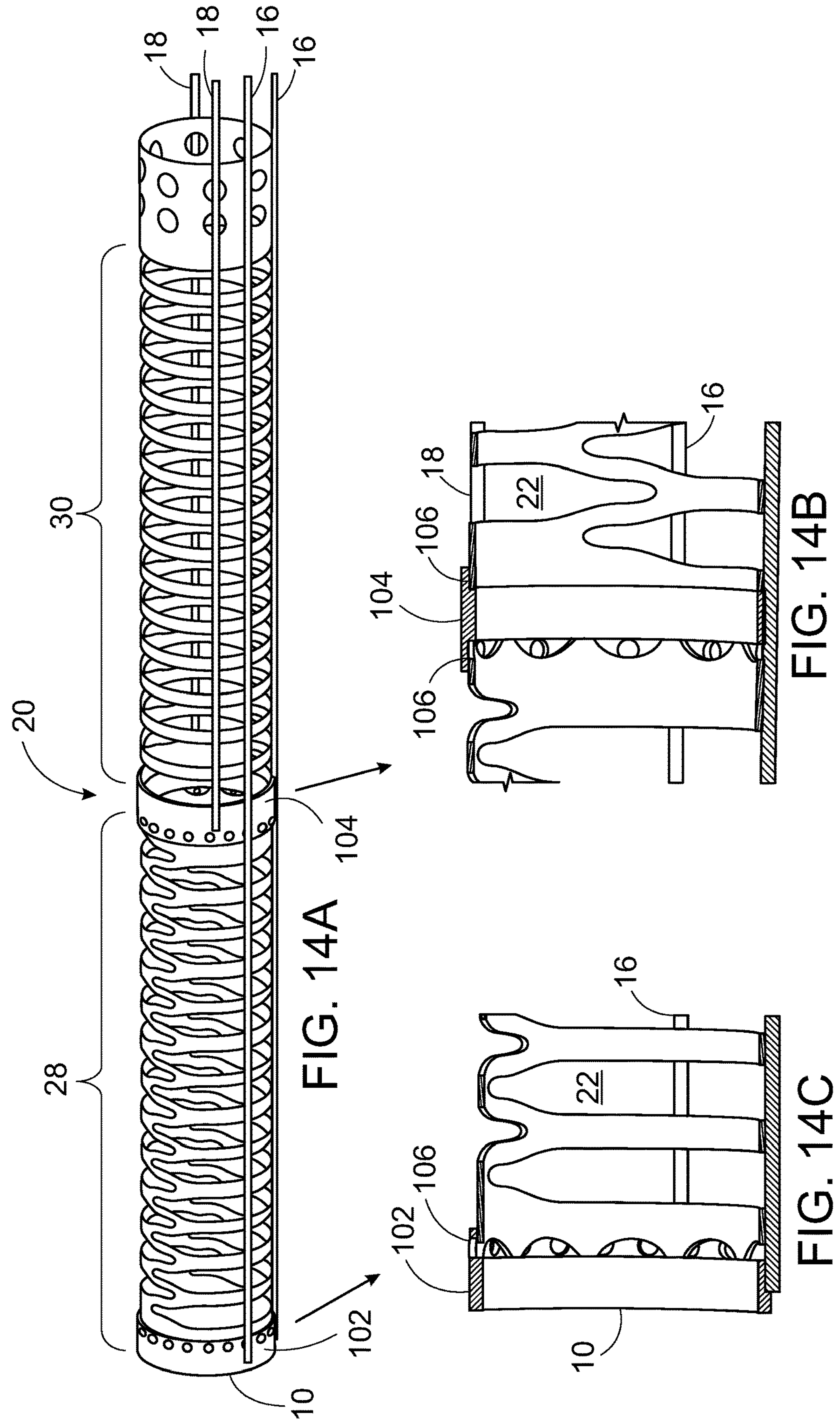
FIGS. 14A, 14B and 14C show another example for the elastic element.

Another example for the elastic element 20 is shown in FIG. 14A, with enlarged sectional views of certain parts shown in FIGS. 14B and 14C. This version is optimised for use of a reinforced polymer material for the first flexible section 28 and the use of a metal for the second flexible section 30, and it includes an example of bonding arrangements for coupling together the different parts. The arrangement of the control wires 16, 18, 18' is similar to that in FIG. 13, but it will be appreciated that the differing designs of elastic element 20 may be used with various arrangements of the control wires 16, 18, 18'. In order to join the various parts, and to provide for a secure attachment of the control wires 16, 18. 18' the introducer may include fixing rings 102, 104 as shown, with greater detail being visible in FIGS. 14B and 14C. Similar rings 102. 104 could be used with the elastic elements 20 with alternative designs for the cut patterns disclosed herein. There is a distal fixing ring 102 at the distal end 10 for enclosing the end of the first flexible section 28 and for securing holding the twisting control wires 16 at the distal end 10. In addition there is an intermediary fixing ring 104 between the first flexible section 28 and the second flexible section 30. Both fixing rings 102, 104 may be a relatively rigid material, for example stainless steel with a greater thickness than the thickness of the metal used for second flexible section 30. The fixing rings 102,104 have indent sections 106 for receiving and overlapping with the first flexible section 28 and the second flexible section 30, as well as openings to provide good interconnection with the relatively soft elastic material 32, 34 around the elastic element 20. As with the other examples, there can be a coil placed around the elastic element 20, optionally embedded in the relatively soft elastic material, which can be used to reduce the risk of the control wires pulling through the elastic material, and escaping the surface of the tube, when it is deflected.

Reinforced braided micro tubes, or other composite tubing, could be additionally or alternatively used to contain the control wires for the same reason. The control wires may be housed within the reinforced braided micro tubes. This may also reduce any associated friction between the control wires and the elastic element 20 during actuation of the control wires, such that smoother and/or finer control of the elastic element 20 is possible.

Figure 15:
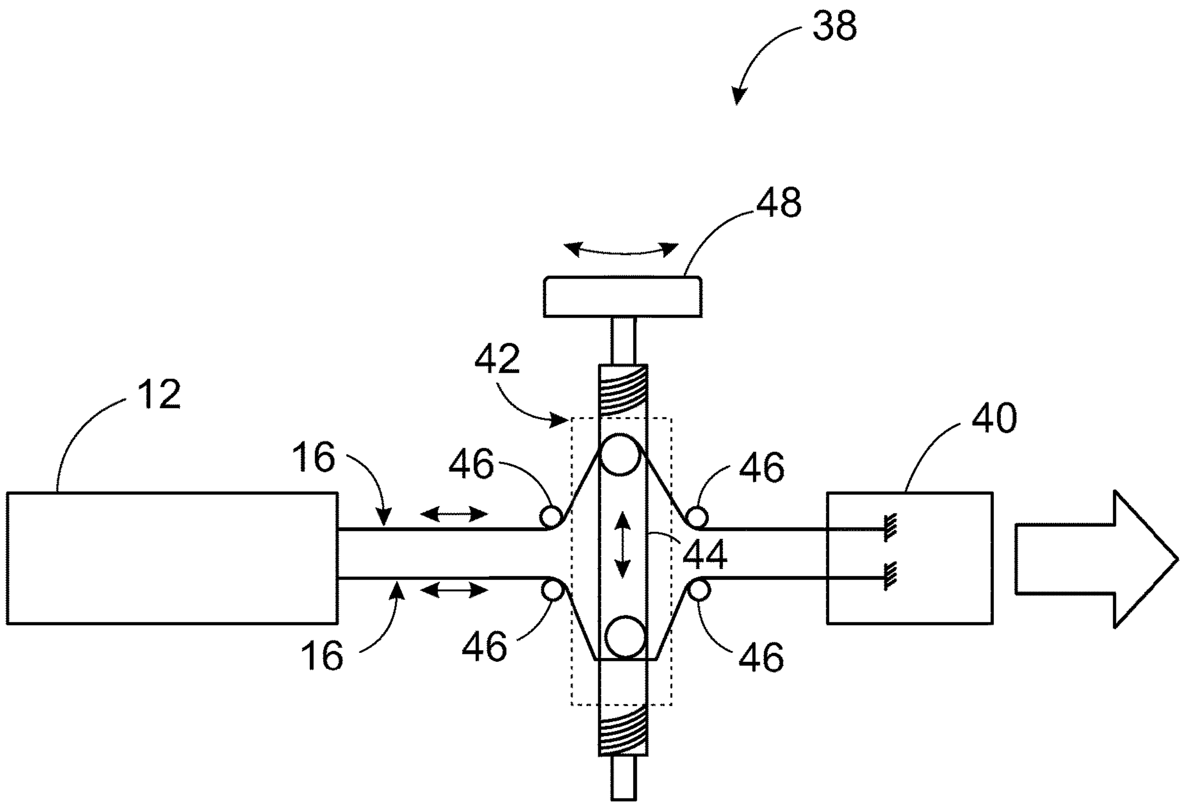
FIG. 15 shows a twisting control mechanism for controlling the tension in twisting control wires.

The tension in the control wires 16, 18, 18' can be varied via a controller. The controller in this example includes a twisting control mechanism 38 as shown in FIG. 15, and this is for varying the tension in the twisting control wires 16. The controller also includes a further control device (not shown) for applying tension to the steering control wires 18, 18'. The twisting control mechanism 38 comprises a tensioner 40 for applying tension to both of the pair of twisting control wires 16, and a tension balancer 42 for varying the relative tension of the two twisting control wires 16. The tensioner 40 applies a tensioning force along the length of the two twisting control wires 16 via a pulling force applied to a proximal end of each wire 16. The tension balancer 42 varies the relative tension by adjusting a lateral force on each of the two twisting control wires, i.e. a force applied in a direction that extends perpendicular to the longitudinal extent of the wires at the controller and using the principle of bow tension as seen in FIG. 15. The variation in lateral displacement of the twisting control wires 16 changes the longitudinal tension in the wires.

The twisting control mechanism 38 includes a sledge 44 in contact with both of the twisting control wires 16 and lateral restraints 46 that are spaced apart from the sledge in the longitudinal direction of the wires 16. The lateral restraints 46 restrict lateral movement of the wires 16 in the direction of the lateral force applied by the tension balancer, such that the lateral force from the tension balancer 42 distorts the respective twisting control wire 16 into a V-shape as shown. A sliding motion of the sledge 44 in a first direction will increase a lateral displacement of the first twisting control wire 16 whilst decreasing the lateral displacement of the second twisting control wire 16, and where a sliding motion of the sledge 44 in a second direction will increase a lateral displacement of the second twisting control wire 16 whilst decreasing the lateral displacement of the first twisting control wire 16. The sledge 44 is actuated by a control input 48 in the form of a knob that turns a screw thread in order to slide the sledge 44 in the first direction or the second direction.

When one of the twisting control wires 16 has more tension than the other then the flexible distal portion 14 will twist in one direction, and if the relative tension is reversed then it should twist in the opposite direction. If both are pulled equally the flexible distal portion 14 will deflects without twist. The twisting motion can be used to align the device with the mitral plane.

Figure 16:
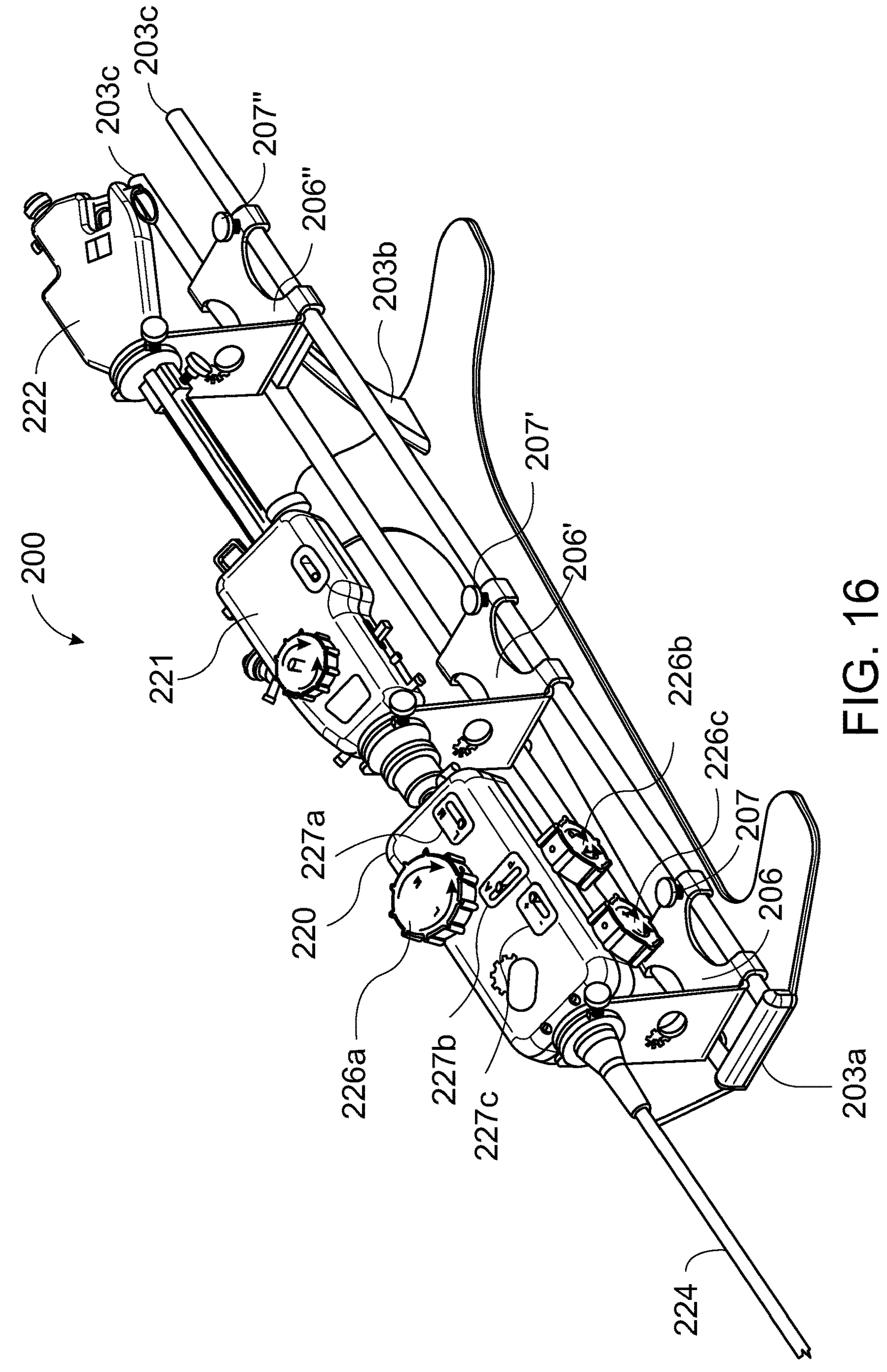
FIG. 16 is a perspective view of a handle for operating the steerable catheter as well as the associated catheter device.

FIG. 16 shows a device handle 200 for operating and controlling the catheter device as well as the steerable introducer. The device handle 200 comprises a rack 202, on which one or more rack wagons 206, 206', 206" may be mounted. The rack wagons 206, 206', 206" provide a number of supports to which one or more operating handles 220, 221, 222 may be mounted. The operating handles 220, 221, 222 in turn are used to actuate one or more pullwires housed within a pullwire sheath 224 of the catheter device, to control the functionality of the catheter device 2 as described above. The pullwire sheath 224 may be a 24 French catheter. It will however be appreciated that other sizes of catheter could be used.

The rack 202 shown in FIG. 16 comprises a base structure to which at least two supports are mounted. A first support 203*a* is located at a distal end of the rack 202, whilst a second support 203*b* is located at a proximal end of the rack 202. The supports 203*a*, 203*b* provide a mounting surface for a rail 203*c*. Whilst the second support 203*b* is seen to be at a greater raised height from the surface of the rack 202 than the first support 203*a*, it will be readily understood that various support shapes and structures may be utilised to provide the mounting surface for the rail 203*c*. The rail 203*c* provides a support structure to which the rack wagons 206, 206', 206" may be slidably mounted to. It will be readily appreciated that a number of suitable arrangements of the rack 202 may be implemented in the device handle 200 of the catheter device. For example, the rack 202 may comprise more than two supports 203*a*, 203*b*, and the rail 203*c* may take on a number of configurations as long as the rack wagons 206, 206', 206" may be slidably mounted on the rail 203*c*.

Whilst three rack wagons 206, 206', 206" are shown in FIG. 16, any number of rack wagons 206, 206', 206" may be utilised in the device handle 200 as appropriate. Focusing now on a single rack wagon 206, the rack wagon 206 is formed from a single piece of sheet metal. The rack wagon 206 comprises a bent shape, with a first portion of the rack wagon 206 being perpendicular to a second portion of the rack wagon 206. The first rack portion may lie in a plane parallel to that of the rail 203*c*, and comprise a number of legs which allow the rack wagon 206 to be slidably mounted onto the rail 203*c*. A thumb screw 207 may then be used to clamp the rack wagon 206 to the rail 203*c*, to prevent the rack wagon 206 from moving from its desired position. Thus during assembly (and vice versa for disassembly) of the delivery handle 200 shown in FIG. 16, the rack wagons 206, 206', 206" may be slid on to the rail 203*c* from the proximal end of the rack 202. Thumb screws 207, 207', 207" are then tightened to clamp the rack wagons 206, 206', 206" at their respective locations. Advantageously, this allows the rack wagons 206, 206', 206" to be mounted and/or removed from the rack 202 without using any specialised tools. The components of the device handle 200 may then be taken for sterilisation following any operation or procedure with relative ease.

Still with reference to a single rack wagon 206, a second portion of the single piece of sheet metal may be perpendicular to the first portion. The second portion may comprise, at its end furthest from the bend in the rack wagon 206, a slot of semi-circular, ovoid or any other suitable cross section to which a number of clamping devices may be attached. The clamping devices may comprise a number of washers, O-rings and/or clamps which themselves provide support for the pullwire sheath 224 and the operating handles 220, 221, 222.

Turning now to the operating handles 220, 221 and 222 shown in FIG. 16, a number of spacers and washers, O-rings and/or clamps keep the operating handles 220, 221, 222 in their desired positions rigidly along the pullwire sheath 224. The spacers and washers, O-rings and/or clamps may themselves also be disposed about the pullwire sheath 224. Whilst three delivery handles 220, 221, 222 are shown mounted to the delivery handle 200, it will be readily appreciated that any number of delivery handles 220, 221, 222 may be mounted in the delivery handle 200 to achieve the desired operation of the catheter device and the steerable introducer.

Focusing on the operating handle 220 shown mounted between the first rack wagon 206 and the second rack wagon 206', the operating handle 220 may comprise a number of gears and/or dials 226*a*, 226*b*, 226*c*. Each gear and/or dial 226*a*, 226*b*, 226*c* may control the actuation of a pullwire disposed in the pullwire sheath 224. The operating handle 220 is used to control the steering action of the steerable introducer, for example with the pullwire actuated by any one of the gears and/or dials 226*a*, 226*b*, 226*c* being a part of a steering control mechanism or the twisting control mechanism 38 for the steerable introducer. Thus, the dial 226*c* may control the tension in the steering control wires 18, 18', whereas the dial 226*b* may control the tension in the twisting control wires 16.

The arrangement of the operating handles 220, 221, 222 can be changed to suit the user preference and to align with a desired procedure. For example, the pullwire actuated by any one of the gears and/or dials 226*a*, 226*b*, 226*c* could alternatively be, but not limited to, the pullwire 204 operating a hinge element of the catheter device and so on. Similarly, the gears, dials and other control inputs for the operating handles 221 and 222 may control various elements of the catheter device. In one arrangement, the proximal operating handle 220 controls the steerable introducer as well as advancement of the catheter device, the middle operating handle 221 controls various functions of the catheter device such as functions relating to grasping the leaflet and implantation of a leaflet anchor, and the proximal operating handle 222 controls further operations linked to implantation of an artificial chord, such as adjustment and/or cutting of the chord. In addition, the relative location of the operating handles 220, 221, 222 on their respective rack wagons 206, 206', 206" can be varied to move elements of the catheter device at the distal end of the 24 French 224, for example sliding of the proximal rack wagon 206" may advance a papillary anchor and thereby implant it into the papillary muscle.

To indicate the amount of tension and/or deflection applied to each pullwire controlled by the gears and/or dials 226*a*, 226*b*, 226*c* of the catheter device, a number of indicators 227*a*, 227*b*, 227*c* may also be disposed on an outer surface of the operating handle 220. These may be used as feedback indicators to indicate to the operator of the catheter device 2 how much tension is currently applied to the pullwires, along with their current behaviour/positioning.

Whilst the functionality of the operating handle has only been discussed in relation to a single operating handle 220, it will be readily understood that some or all of the features discussed herein may be applied to the other operating handles 221, 222 of the delivery handle 200.

The controller may be equipped with springs to restrict force applied to the control wires to prevent overloading the wires during articulation, as simultaneous/excessive tension of all wires may collapse the flexible distal portion 14. A constant tension device can be used to ensure a minimum tension at all times and avoid any slack in the control wires 16, 18, 18' as the introducer passes through the body and is curved by external forces.

The invention claimed is:

1. A steerable introducer for a catheter device, the steerable introducer comprising:

a body portion having a longitudinal axis extending from a proximal end of the introducer toward a distal end of the introducer, wherein the body portion comprises a flexible distal portion extending to the distal end;

a hollow within a part of the body portion for holding the catheter device during a procedure to introduce the catheter device into the body;

at least one steering control wire extending axially along the body portion and along at least a part of an axial length of the flexible distal portion;

a pair of twisting control wires extending axially along the body portion and along at least a part of an axial length of the flexible distal portion; and a controller for controlling the tension in the at least one steering control wire and in the pair of twisting control wires;

wherein the at least one steering control wire has a distal end that is fixed to the flexible distal portion at a first point in a first axial and circumferential position on the flexible distal portion, with the introducer being arranged to allow for tension on the at least one steering control wire to cause a curvature of the flexible distal portion; and wherein the pair of twisting control wires each have a distal end, with the twisting control wire distal ends being fixed to the flexible distal portion at second and third points at respective second and third axial and circumferential positions on the flexible distal portion, with the circumferential position of the twisting control wire distal ends being different from each other as well as different from the circumferential position of the steering control wire, and with the introducer being arranged to allow for variations in relative tension between the pair of twisting control wires to cause twisting of the flexible distal portion;

wherein the controller is arranged to control relative tension between the pair of twisting control wires;

wherein the controller includes a twisting control mechanism comprising: a tensioner for applying tension to both of the pair of twisting control wires, and a tension balancer for varying the relative tension of the pair of twisting control wires; and wherein the tension balancer is arranged to vary the relative tension in the pair of twisting control wires by adjusting a lateral force on each wire of the pair of twisting control wires;

wherein the twisting control mechanism includes lateral restraints spaced apart from the tension balancer in a longitudinal direction of the pair of twisting control wires and fixed either side of the tension balancer in the longitudinal direction of the pair of twisting control wires; and wherein the lateral restraints are provided to restrict lateral movement of the pair of twisting control wires in a direction of the lateral force applied by the tension balancer, such that variation in a lateral displacement of each twisting control wire changes a longitudinal tension in said twisting control wire.

2. The steerable introducer as claimed in claim 1, wherein the distal end of the introducer can be moved via a twisting movement simultaneously with a steering movement, so that the distal end may shift out-of-plane from the plane of the curvature and result in tension on the at least one steering control wire alone.

3. The steerable introducer as claimed in claim 1, wherein the axial position of the twisting control wire distal ends is about the same.

4. The steerable introducer as claimed in claim 1, wherein the distal ends of the pair of twisting control wires are separated in their circumferential position by between 5-40% of a circumference of the flexible distal portion.

5. The steerable introducer as claimed in claim 1, wherein a distal segment of the flexible distal portion comprises a reinforced polymer backbone surrounded with an elastic polymer material.

6. The steerable introducer as claimed in claim 1, wherein the tension in the pair of twisting control wires is controlled by the tension balancer through a sledge in contact with both wires of the pair of twisting control wires, where a sliding motion of the sledge in a first direction will increase a lateral displacement of a first twisting control wire of the pair of twisting control wires whilst decreasing the lateral displacement of a second twisting control wire of the pair of twisting control wires, and where a sliding motion of the sledge in a second direction will increase a lateral displacement of the second twisting control wire whilst decreasing the lateral displacement of the first twisting control wire.

7. The steerable introducer as claimed in claim 1, wherein the controller includes control inputs for manual control of the tension in the wires, wherein the control inputs include an input to control relative tension between the pair of twisting control wires via manual user input.

8. The steerable introducer as claimed in claim 1, comprising at least one of:

one or more constant tension device for maintaining a minimum tension on one or more wires of the pair of twisting control wires; and more than one steering control wire to allow for a greater control of a degree of curvature.

9. The steerable introducer as claimed in claim 1, wherein the flexible distal portion is elastically flexible and returns elastically to a resting position when no tension is applied to the at least one steering control wire or the pair of twisting control wires; and wherein the flexible distal portion is arranged to have a curve and a twist in its resting position such that a tension must be applied to one or more wires of the at least one steering control wire in order to move the flexible distal portion into a straight configuration, wherein the flexible distal portion has a resting position that has 20-60% of a curve and twist required for deployment of the catheter device.

10. The steerable introducer as claimed in claim 1, wherein the flexible distal portion has a different elasticity at different axial positions and/or different elasticity with respect to bending in different directions.

11. The steerable introducer as claimed in claim 1, wherein the flexible distal portion has a first flexible section at the distal end of the introducer and a second flexible section between the first flexible section and the main body, with each flexible section having a different elasticity.

12. The steerable introducer as claimed in claim 11, wherein at least one of:

the first flexible section is more flexible than the second flexible section;

the first flexible section and the second flexible section comprise elastic materials of differing stiffness and/or thickness, with the differences in the elastic materials contributing to the different elasticity of the first flexible section and the second flexible section;

the first flexible section comprises a polymer material and the second flexible section comprises an elastic metal material; or the first flexible section is arranged for a greater ease of twisting, whilst the second flexible section is stiffer when twisted, wherein the second flexible section has a first stiffness with respect to bending forces applied in a first direction and a second, different, stiffness with respect to bending forces applied in a second direction such that the second flexible section is relatively more flexible in a side to side direction and relatively more rigid in a front to back direction, whereas the first flexible section is able to bend relatively easily in all directions.

13. The steerable introducer as claimed in claim 1, wherein the flexible distal portion comprises elastic elements including one or more elements having the form of a tube with cuts permitting bending of the tube, and wherein the elastic element(s) comprise differing geometries of cuts at different points along the length of the flexible distal portion; and wherein the tube is a tube that has been formed by heat setting a metal, with the heat setting being used in order that the tube has a resting position that incorporates some curve and twist.

14. The steerable introducer as claimed in claim 1, wherein the lateral restraints include fixed restraints for preventing movement of the at least one twisting control wire at corresponding points in the direction of the lateral force applied by the tension balancer, such that the lateral force from the tension balancer distorts a respective twisting control wire of the pair of twisting control wires into a V-shape.

15. The steerable introducer as claimed in claim 1, wherein the lateral restraints are positioned between a proximal end and a distal end of the pair of twisting control wires.

16. The steerable introducer as claimed in claim 15, wherein the proximal end of the pair of twisting control wire is coupled to the tensioner.

17. The steerable introducer as claimed in claim 1, wherein the twisting control mechanism includes second lateral restraints spaced apart from the tension balancer and the tensioner in a longitudinal direction of a second twisting control wire of the pair of twisting control wires, where a first restraint of the second lateral restraints is between the tension balancer and the tensioner and a second restraint of the second lateral restraints is distal of the tension balancer along the longitudinal direction.

18. A cardiac treatment apparatus comprising:

a steerable introducer as claimed in claim 1; and a catheter device for performing an operation within a heart, wherein the catheter device is housed within the hollow of the steerable introducer.

19. A method of manufacture of a steerable introducer as claimed in claim 1, the method comprising:

providing the body portion with the flexible distal portion, including providing the hollow within a part of the body portion for holding the catheter device; and arranging the flexible distal portion to allow for curvature and twisting thereof by:

fitting of the at least one steering control wire and the pair of twisting control wires, including attaching the at least one steering control wire in a position extending axially along the body portion and along at least a part of an axial length of the flexible distal portion, and attaching the pair of twisting control wires in a position extending axially along the body portion and along at least a part of an axial length of the flexible distal portion;

fixing a distal end of the at least one steering control wire to the flexible distal portion at a first point in a first axial and circumferential position on the flexible distal portion, with the introducer hence being arranged to allow for tension on the at least one steering control wire to cause a curvature of the flexible distal portion; and fixing the distal ends of the pair of twisting control wires to the flexible distal portion at second and third points at respective second and third axial and circumferential positions on the flexible distal portion, with the circumferential position of the twisting control wire distal ends being different from each other as well as different from the circumferential position of the steering control wire, and with the introducer hence being arranged to allow for variations in relative tension between the pair of twisting control wires to cause twisting of the flexible distal portion.

20. Use of the steerable introducer of claim 1 for introducing a catheter device into a heart.

* * * * *